United States Patent [19]

Borror et al.

[11] 4,311,839
[45] Jan. 19, 1982

[54] BENZISOTHIAZOLE AND NAPHTHO-1,2-THIAZINE COMPOUNDS

[75] Inventors: Alan L. Borror, Lexington; Louis Cincotta; James W. Foley, both of Andover; Marcis M. Kampe, Brookline, all of Mass.

[73] Assignee: Polaroid Corporation, Cambridge, Mass.

[21] Appl. No.: 219,214

[22] Filed: Dec. 22, 1980

Related U.S. Application Data

[62] Division of Ser. No. 836,008, Sep. 23, 1977.

[51] Int. Cl.$^3$ .................. C07D 417/12; C07D 275/06
[52] U.S. Cl. ........................... 544/135; 544/33; 544/58.7; 544/69; 544/229; 544/368; 546/14; 546/94; 546/198; 548/110; 548/207; 260/245.5
[58] Field of Search .................. 544/33, 69, 58.7, 135, 544/229, 368; 548/207, 110; 546/198, 14, 94; 260/245.5

[56] References Cited

PUBLICATIONS

Mustafa et al., *J. Chem. Soc.*, (1952) pp. 1339–1340.
Abramovitch et al., *J. Chem. Soc.*, Perkins Trans. I, 22, (1974), pp. 2589–2594.
Dutt, *J. Chem. Soc.*, 121, pp. 2389–2394 (1922).
Houben-Weyl, *Met. der Org. Chemie*, vol. 13, (1970) pp. 189–190.

Beilstein's, *Handbuch der Organ. Chemie*, vol. 27, p. 534.

*Primary Examiner*—Henry R. Jiles
*Assistant Examiner*—R. W. Ramsuer
*Attorney, Agent, or Firm*—Sybil A. Campbell

[57] ABSTRACT

In one aspect, this invention relates to a method of synthesizing certain 3-(4'-OP-carbocyclic aryl)-3-(carbocyclic aryl)-2,3-dihydrobenz[d]isothiazole-1,1-dioxides (and -2,3-dihydronaphtho[1,8-de]-1,2-thiazine-1,1-dioxides) by reacting (a) a 3-(4'-OP-carbocyclic aryl)-benz[d]isothiazole-1,1-dioxide wherein P is a protecting group or a 3-(4'-OP-carbocyclic aryl)-naphtho[1,8-de]-1,2-thiazine-1,1-dioxide wherein P is a protecting group and (b) a carbocyclic aryllithium compound to give (c) the corresponding 3-(4'-OP-carbocyclic aryl)-3-(carbocyclic aryl)-2,3-dihydrobenz[d]-isothiazole-1,1-dioxide or the corresponding 3-(4'-OP-carbocyclic aryl)-3-(carbocyclic aryl)-2,3-dihydronaphtho-[1,8-de]-1,2-thiazine-1,1-dioxide.

In another aspect, the present invention relates to the 3,3-disubstituted-2,3-dihydrobenz[d]isothiazole-1,1-dioxides and the 3,3-disubstituted-2,3-dihydronaphtho[1,8-de]-1,2-thiazine-1,1-dioxides produced by the above-described method provided the 3,3 substituents are different, which compounds are useful in the synthesis of phenol and 1-naphthol sulfam(na)phthaleins employed, for example, as photographic optical filter agents and filter agent precursors.

39 Claims, No Drawings

BENZISOTHIAZOLE AND NAPHTHO-1,2-THIAZINE COMPOUNDS

This is a division of application Ser. No. 836,008, filed Sept. 23, 1977.

BACKGROUND OF THE INVENTION

1. Field of the Invention

This invention relates to certain 3,3-disubstituted-2,3-dihydrobenz[d]isothiazole-1,1-dioxides and to certain 3,3-disubstituted-2,3-dihydronaphtho[1,8-de]-1,2-thiazine-1,1-dioxides useful in the preparation of phenol and 1-naphthol sulfamphthaleins and sulfamnaphthaleins and to the preparation of said 3,3-disubstituted compounds.

2. Description of the Prior Art

Various procedures have been reported for synthesizing 3-substituted-benz[d]isothiazole-1,1-dioxides and 3,3-disubstituted-2,3-dihydrobenz[d]isothiazole-1,1-dioxides from saccharin (3-oxo-2,3-dihydrobenz[d]isothiazole-1,1-dioxide) and from saccharin pseudo-chloride (3-chlorobenz[d]isothiazole-1,1-dioxide). As reported by A. Mustafa et al, *J. Chem. Soc.*, 1952, p. 1339, the treatment of saccharin pseudo-chloride with excess phenylmagnesium bromide gave the corresponding 3,3-diphenyl-2,3-dihydrobenz[d]isothiazole-1,1-dioxide in almost quantitative yield. Methyl-, ethyl-, n-propyl- and n-butylmagnesium halides were reported by these authors to react analogously. R. A. Abramovitch et al, *J. Chem. Soc., Perkin Trans I*, 1974(22), p. 2589, reviewed and reinvestigated reagents and found that either the 3-alkyl (or 3-aryl)-benz[d]isothiazole-1,1-dioxide and/or the open-chain tertiary alcohol, o-$CR_2OH$ benzenesulfonamide wherein R is alkyl (or aryl) were obtained with one exception. When saccharin was treated with an excess of phenylmagnesium bromide in boiling tetrahydrofuran, 3,3-diphenyl-2,3-dihydrobenz[d]isothiazole-1,1-dioxide was obtained as the minor product together with the open-chain tertiary alcohol.

R. A. Abramovitch et al also investigated the reaction of saccharin and saccharin pseudo-chloride with organolithium compounds and found that the reaction of saccharin with alkyl- and aryllithium compounds, such as, n-butyllithium and p-methoxyphenyllithium in tetrahydrofuran at $-78°$ C. gave the corresponding 3-substituted-benz[d]isothiazole-1,1-dioxide, exclusively. In addition to this general method for synthesizing 3-alkyl (or 3-aryl)-benz[d]isothiazole-1,1-dioxides, the authors reported that the reaction of the pseudo-chloride with organolithium compounds, such as, n-butyllithium in tetrahydrofuran at $-78°$ C. gave the corresponding 3,3-disubstituted-2,3-dihydrobenz[d]isothiazole-1,1-dioxide as the major product.

Besides the reactions with Grignard and organolithium reagents, Friedel-Crafts reactions with the saccharins also have been disclosed. Dutt, *J. Chem. Soc.*, 121, p. 2389 (1922) reported the condensation of saccharin with aromatic amines and phenols in the presence of concentrated sulfuric acid and also in the presence of fused zinc chloride. The resulting condensation products with saccharin were named "sulfamphthaleins" by analogy to "phthaleins" and "sulfonephthaleins". Though the structure of 3,3-di(4'-hydroxyphenyl)-2,3-dihydrobenz[d]isothiazole-1,1-dioxide (named "phenolsulfamphthalein") was assigned to the condensation product obtained with saccharin and phenol, it has been determined that the compound corresponding to the proposed structure has properties different from those reported, for example, colorless rather than pink in alkali and also, that the compound corresponding to the structure given could not be synthesized by repeating the procedures reported by Dutt.

Copending U.S. Patent Application Ser. No. 836,010 of Stanley M. Bloom, Alan L. Borror and James W. Foley filed concurrently herewith is directed to a method of synthesizing phenol and 1-naphthol sulfamphthaleins and sulfamnaphthaleins possessing a carbonyl group in the 2-position of the sulfam(na)phthalein ring. Depending upon the carbonyl group and the phenolic and/or naphtholic substituents, the products of the synthesis may be employed as pH-sensitive indicator dyes, antihalo dyes or photographic optical filter agents. As disclosed and claimed therein, the method of preparing these compounds comprises reacting a 3-(4'-OP-carbocyclic aryl)-3-(carbocyclic aryl)-2,3-dihydrobenz[d]isothiazole-1,1-dioxide (or -2,3-dihydronaphtho[1,8-de]-1,2-thiazine-1,1-dioxide) wherein P is a protecting group with a carboxylic acid halide to yield the corresponding 2-carbonyl derivative followed by removing the protecting group with weak acid to yield the product.

The present invention is concerned with 3-(4'-OP-carbocyclic aryl)-3-(carbocyclic aryl)-2,3-dihydrobenz[d]isothiazole-1,1-dioxides (and -2,3-dihydronaphtho[1,8-de]-1,2-thiazine-1,1-dioxides) useful as starting materials in the aforementioned synthesis and to the preparation of said isothiazole and said 1,2-thiazine-1,1-dioxides.

SUMMARY OF THE INVENTION

It is, therefore, the primary object of the present invention to provide certain 3,3-disubstituted-2,3-dihydrobenz[d]isothiazole-1,1-dioxides and certain 3,3-disubstituted-2,3-dihydronaphtho[1,8-de]-1,2-thiazine-1,1-dioxides useful in the preparation of phenol and 1-naphthol and sulfam(na)phthaleins.

It is another object of the present invention to provide a method of preparing said 3,3-disubstituted isothiazole and 1,2-thiazine-1,1-dioxides.

Other objects of this invention will in part be obvious and will in part appear hereinafter.

This invention accordingly comprises the process involving the several steps and the relation and order of one of more of such steps with respect to each of the others and the product possessing the features, properties and the relation of elements which are exemplified in the following detailed disclosure and the scope of the application of which will be indicated in the claims.

According to the present invention, 3-(4'-OP-carbocyclic aryl)-3-(carbocyclic aryl)-2,3-dihydrobenz[d]isothiazole-1,1-dioxides are prepared by reacting (a) a 3-(4'-OP-carbocyclic aryl)-benz[d]isothiazole-1,1-dioxide wherein P is a protecting group and (b) a carbocyclic aryllithium compound to give (c) the corresponding 3-(4'-OP-carbocyclic aryl)-3-(carbocyclic aryl)-2,3-dihydrobenz[d]isothiazole-1,1-dioxide. The 1,2-thiazine-1,1-dioxides are prepared in the same manner except that a 3-(4'-OP-carbocyclic aryl)-naphtho[1,8-de]-1,2-thiazine-1,1-dioxide is reacted with the carbocyclic aryllithium compound.

The subject method is applicable to the synthesis of 3,3-disubstituted-2,3-dihydrobenz[d]isothiazole-1,1-dioxides and 3,3-disubstituted-2,3-dihydronaphtho[1,8-de]-1,2-thiazine-1,1-dioxides wherein one of the 3,3 substituents is a 4'-OP-phenyl moiety, unsubstituted or substituted with one or more groups compatible with organometallic reagents, or a 4'-OP-naphthyl moiety, unsubstituted or substituted with one or more groups compatible with organometallic reagents. The other of the 3,3 substituents may be the same or different. The compounds of the present invention comprise the above-denoted compounds wherein the 3,3 substituents are different. Such compounds wherein the 3,3 substituents are the same comprise the subject matter of copending U.S. Patent Application Ser. No. 836,004 of Stanley M. Bloom, Alan L. Borror and James W. Foley filed concurrently herewith.

For a fuller understanding of the nature and objects of the present invention, reference should be had to the following detailed description.

DESCRIPTION OF THE PREFERRED EMBODIMENTS

Specifically, the method of the present invention comprises reacting (a) a compound of the formula

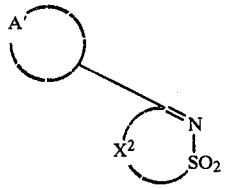

wherein A' is a 4'-OP-1'-phenyl moiety, unsubstituted or substituted with one or more substituents compatible with organommetallic reagents, the same or different, or a 4'-OP-1'-naphthyl moiety, unsubstituted or substituted with one or more substituents compatible with organometallic reagents, the same or different; P is a protecting group; and $X^1$ represents the atoms necessary to complete a benz[d]isothiazole-1,1-dioxide moiety or a naphtho[1,8-de]-1,2-thiazine-1,1-dioxide moiety and (b) a compound selected from phenyllithium, unsubstituted or substituted with one or more substituents compatible with organometallic reagents, the same or different, and naphthyllithium, unsubstituted or unsubstituted with one or more substituents compatible with organometallic reagents, the same or different, in an inert organic solvent at a temperature of about 50° C. or below to give (c) the compound having the formula

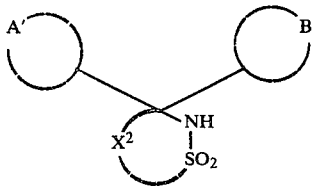

wherein A' is a 4'-OP-1'-phenyl moeity, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; B is a phenyl moiety, unsubstituted or substituted with one or more substituents compatible with organometallic reagents, the same or different, or a naphthyl moiety unsubstituted or substituted with one or more substituents compatible with organometallic reagents, the same or different; P is a protecting group; and $X^2$ represents the atoms necessary to complete a 2,3-dihydrobenz[d]isothiazole-1,1-dioxide moiety or a 2,3-dihydronaphtho[1,8-de]-1,2-thiazine-1,1-dioxide moiety.

The above reaction scheme is illustrated below using as specific reactants, 3-(3'-5'-dimethyl-4'-methoxymethoxy-1'-phenyl)benz[d]isothiazole-1,1-dioxide and N-(p-Li-phenyl)morpholine.

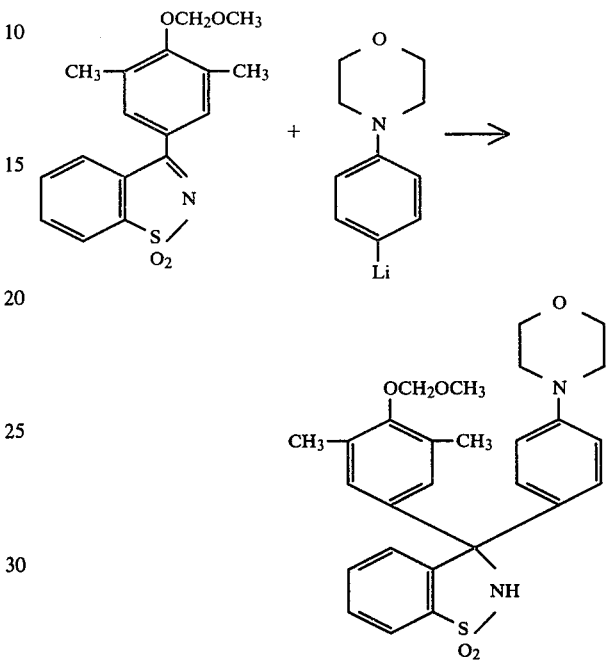

The blocked compounds produced in accordance with the subject method may be symmetrical, i.e., sulfam(na)phthaleins in which the A' and B moieties are identical, or they may be unsymmetrical or mixed. When unsymmetrical, the A' and B moieties would be derived from, for example, a blocked phenol, but each moiety would contain differrent substituents or would contain the same substituents in different positions or one moiety would be substituted and the other unsubstituted. The term "mixed" is intended to denote compounds where the A'moiety, for example, is derived from a blocked phenol and the B moiety is derived from, for example, a blocked 1-naphthol.

The substituents selected for the A' and/or B moieties and, if desired, for the sulfam(na)phthalein moiety should be stable to organometallic reagents, such as, lithium and Grignard reagents and include substituents capable of being blocked during the synthesis by a protecting group that can be subsequently removed under weakly acid conditions simultaneously with the protecting group P used to block the functional -OH of the 4'-hydroxyphenyl or 4'-hydroxynaphthyl moiety.

By "sulfamphthalein" is intended a 2,3-dihydrobenz[d]isothiazole-1,1-dioxide moiety and by "sulfamnaphthalein" is intended a 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-e]-1,2-thiazine-1,1-dioxide ring-closing moieties are illustrated below:

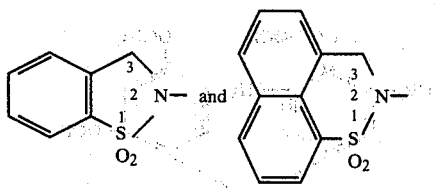

Typical of the sulfam(na)phthaleins that may be prepared according to the present invention are those represented by the following formula:

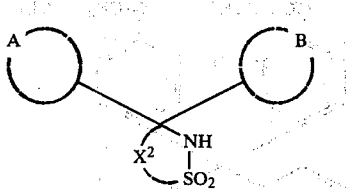

wherein A' is a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; B is a phenyl moiety, unsubstituted or substituted with one or more substituents compatible with organometallic reagents, the same or different, or a naphthyl moiety, unsubstituted or substituted with one or more substituents compatible with organometallic reagents, the same or different; P is a protecting group; and $X^2$ represents the atoms necessary to complete a 2,3-dihydrobenzo[d]isothiazole-1,1-dioxide moiety or a 2,3-dihydronaphtho[1,8-de]-1,2-thiazine-1,1-dioxide moiety.

Typical substituents compatible with or capable of being protected to be compatible with organometallic reagents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenylhexyl and phenyldodecyl; alkoxy, such as, methoxy, ethoxy, butoxy, octadecyloxy, 1-ethoxy-2-(β-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichloromethyl; sulfonamido (-NH-SO₂R° wherein R° is alkyl, aryl, alkaryl or aralkyl); sulfamoyl (-SO₂-NH-R° wherein R° has the same meaning given above); acyl

(—CR° wherein R° has the same meaning given above); sulfonyl (-SO₂-R° wherein R° has the same meaning given above); sulfo; cyano, carboxy, hydroxy; and amino including mono- and disubstituted amino (-NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino or a fused heterocyclic ring system, e.g., quinolizidine).

In a preferred embodiment the method of the present invention comprises reacting (a) a compound of the formula

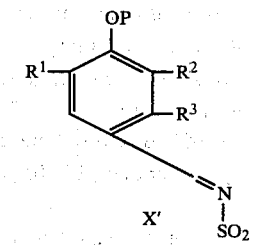

wherein P is a protecting group; $R^1$ and $R^2$ each are selected from hydrogen, alkyl, alkoxy, chloro and fluoro; $R^3$ is hydrogen, alkyl, alkoxy or —OP; $R^2$ and $R^3$ taken together represent the carbon atoms necessary to complete a fused benzene ring and X' represents the atoms necessary to complete benz[d]isothiazole-1,1-dioxide or naphtho[1,8-de]-1,2-thiazine-1,1-dioxide and (b) a compound having the formula

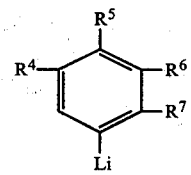

wherein $R^4$ and $R^6$ each are selected from hydrogen, alkyl, alkoxy, chloro and fluoro; $R^5$ is hydrogen, alkyl, alkoxy, —$OP^I$ wherein $P^I$ is a protecting group, —N,-N—(dialkyl)amino, —N,N—(w-$R^8$alkyl)₂amino wherein $R^8$ is halo or —$OP^{II}$ wherein $P^{II}$ is a protecting group, —NHCOCH₃, piperidino, pyrrolidino, N-methylpiperazino, morpholino, thiomorpholino or tetrahydro-2H,4H,1,3,6-dioxazocino; $R^7$ is hydrogen, alkyl, alkoxy or —$OP^{III}$ wherein $P^{III}$ is a protecting group usually the same as $P^I$ or $P^{II}$; $R^6$ and $R^7$ taken together represent the carbon atoms necessary to complete a fused benzene ring; and $R^4$, $R^5$ and $R^6$ taken together represent the atoms necessary to complete a fused [ij]quinolizidine ring in an inert organic solvent at a temperature between about −80° C. and 50° C. to give (c) the compound having the formula

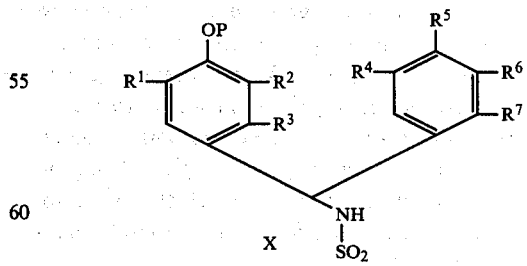

wherein P, $R^1$, $R^2$, $R^3$, $R^4$, $R^5$, $R^6$ and $R^7$ have the same meaning given above and X represents the atoms necessary to complete 2,3-dihydrobenz[d]isothiazole-1,1-dioxide or 2,3-dihydronaphtho[1,8-de]-1,2-thiazine-1,1-dioxide.

Usually, the alkyl and alkoxy substituents comprising R¹, R², R³, R⁴, R⁵, R⁶ and R⁷ are lower alkyl having 1 to 4 carbon atoms, such as, methyl, ethyl, n-propyl, isopropyl and n-butyl and lower alkoxy having 1 to 4 carbon atoms, such as, methoxy, ethoxy, propoxy and butoxy. Also, the alkyl groups of the -N,N-(dialkyl)amino and -N,N-(w-R⁸alkyl)₂-amino substituents usually are lower alkyl having 1 to 4 carbon atoms and R⁸, when halo, is preferably chloro.

In a particularly preferred embodiment, X represents the atoms necessary to complete 2,3-dihydrobenz[d]isothiazole-1,1-dioxide.

As indicated above, in the compounds of the present invention, the 3,3 substituents, i.e., the A' and B moieties are different. The subject compounds may be represented by those shown in formula I above provided said A' and B moieties are different.

In a preferred embodiment, the compounds of the present invention may be represented by the formula

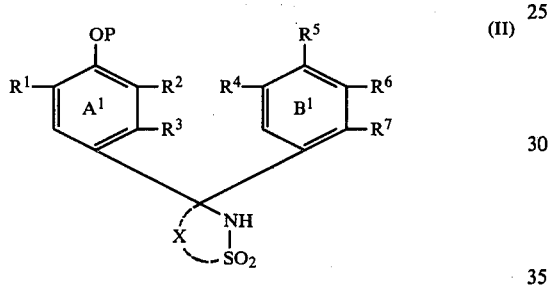
(II)

wherein P is a protecting group, R¹ and R² each are selected from hydrogen, alkyl, alkoxy, chloro and fluoro; R³ is hydrogen, alkyl, alkoxy, or —OP; R² and R³ taken together represent the carbon atoms necessary to complete a fused benzene ring; R⁴ and R⁶ each are selected from hydrogen, alkyl, alkoxy, chloro and fluoro; R⁵ is hydrogen, alkyl, alkoxy, —OP$^I$ wherein P$^I$ is a protecting group, —N,N—(dialkyl)-amino, —N,-N—(w-R⁸alkyl)₂amino wherein R⁸ is halo or —OP$^{II}$ wherein P$^{II}$ is a protecting group, —NHCOCH₃, piperidino, pyrrolidino, N-methylpiperazino, morpholino, thiomorpholino or tetrahydro-2H,4H-1,3,6-dioxazocino; R⁷ is hydrogen, alkyl, alkoxy or —OP$^{III}$ wherein P$^{III}$ is a protecting group usually the same as P$^I$ or P$^{II}$; R⁶ and R⁷ taken together represent the carbon atoms necessary to complete a fused benzene ring; R⁴, R⁵ and R⁶ taken together represent the atoms necessary to complete a fused [ij]quinolizidine ring; and X represents the atoms necessary to complete 2,3-dihydrobenz[d]isothiazole-1,1-dioxide or 2,3-dihydronaphtho[1,8-de]-1,2-thiazine-1,1-dioxide, said A¹ and B¹ moieties being different.

Specific examples of compounds that may be prepared according to the method of the present invention are as follows wherein those possessing 3,3 substituents which are different comprise compounds of the subject invention:

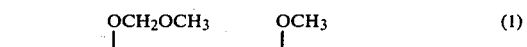
(1)

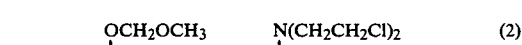
(2)

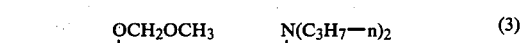
(3)

(4)

(5)

(6)

-continued

-continued
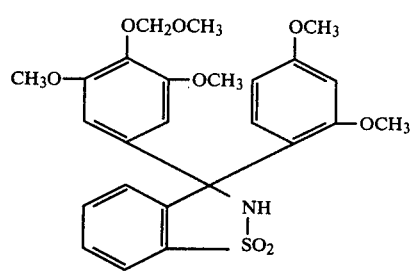 (18)
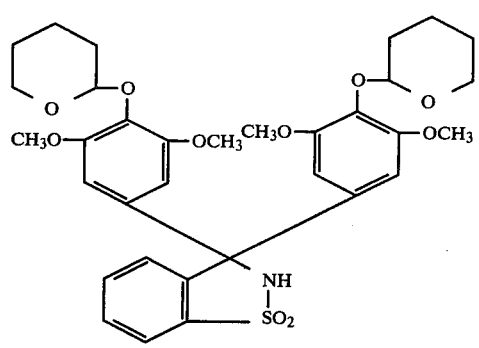 (19)
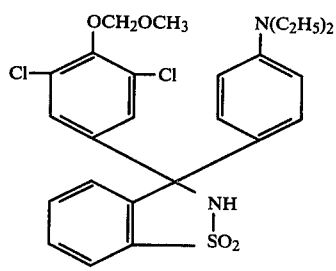 (20)
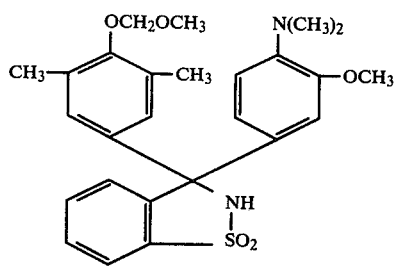 (21)
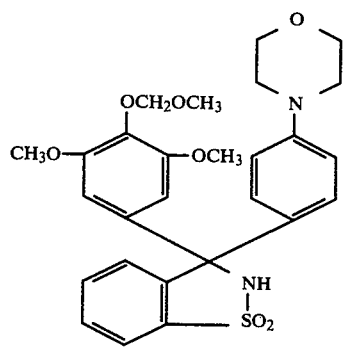 (22)
-continued
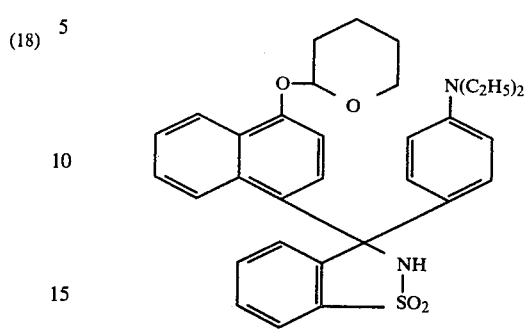 (23)
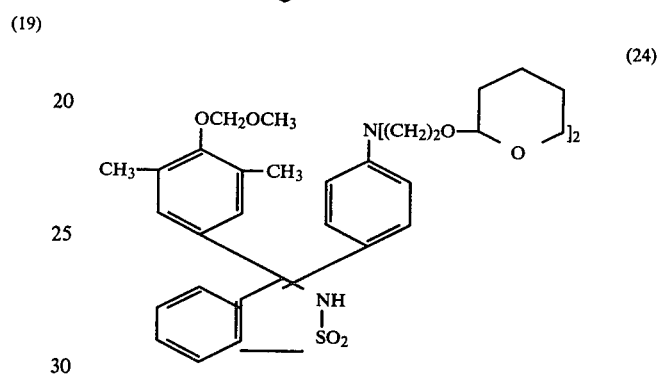 (24)
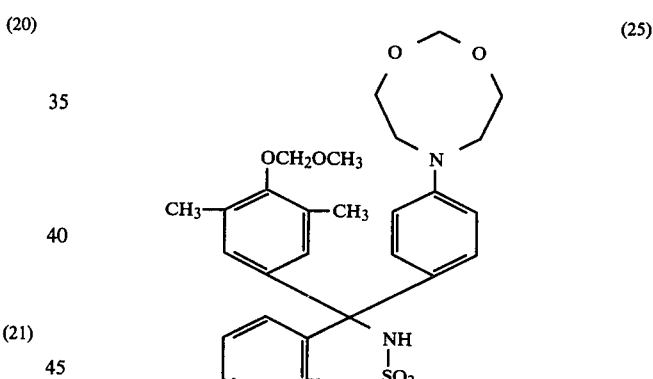 (25)
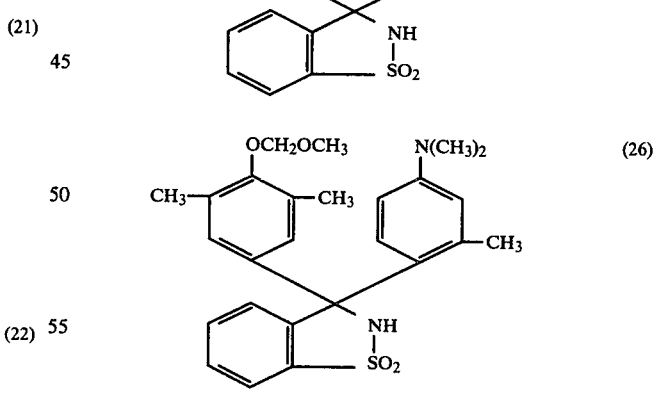 (26)
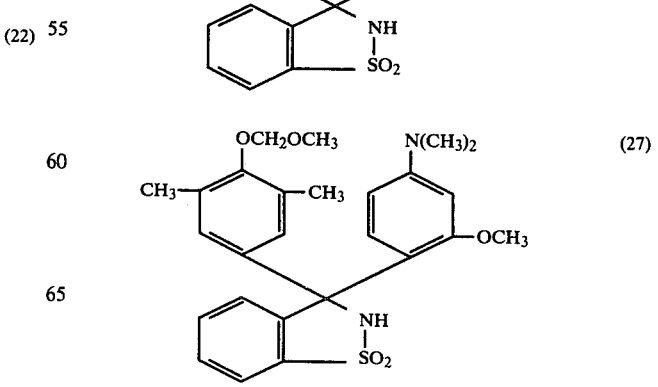 (27)

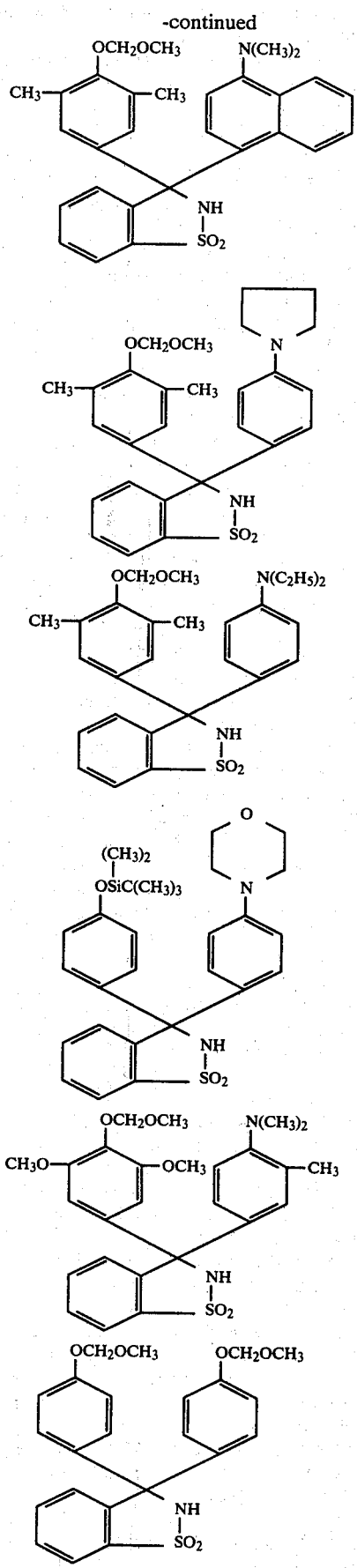
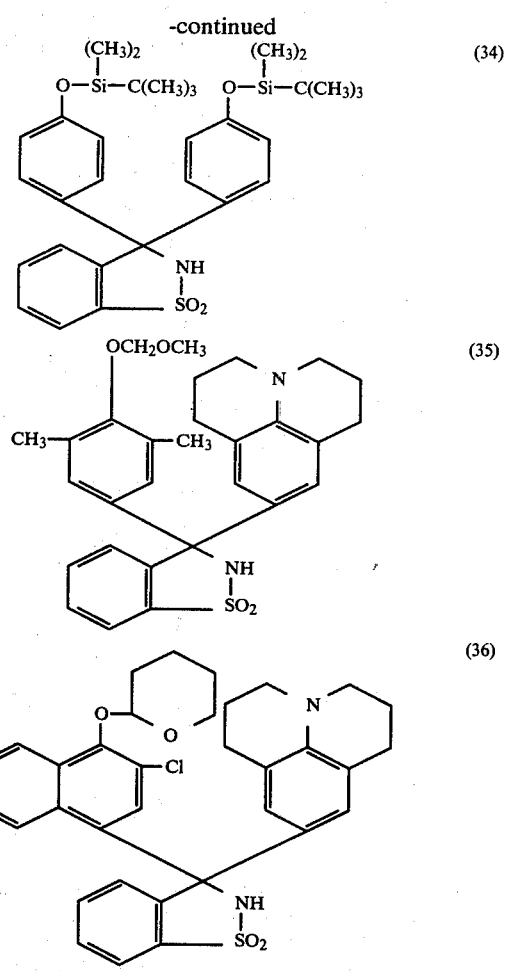

The 3-(4'-OP-1'-phenyl/4'-OP-1'-naphthyl)-benz[d]-isothiazole-1,1-dioxides employed as starting materials in the subject method are prepared by blocking the functional hydroxy group and any substituent group(s), as may be appropriate, of the selected 4-halophenol or 4-halo-1-naphthol and converting the blocked phenol or 1-naphthol to the corresponding Grignard or lithium reagent which is then reacted with a saccharin reagent. The 4-halo substituent may be chloro, bromo or iodo when the lithium reagent is prepared by reacting the blocked phenol or blocked 1-naphthol with lithium metal and is either bromo or iodo when the lithium reagent is made via a lithium exchange reaction using, for example, n-butyllithium. In preparing the Grignard reagent by reacting the blocked phenol or 1-naphthol with magnesium metal, the 4-halo substituent may be chloro, bromo or iodo. The Grignard or lithium reagent thus prepared is then reacted with saccharin, the N-lithium salt of saccharin or saccharin pseudo-chloride to yield the corresponding 3-(4'-OP-1'-phenyl/4'-OP-1'-naphthyl)benz[d]isothiazole-1,1-dioxide. Generally, the Grignard reagent is reacted with the pseudo-chloride, and the lithium reagent is reacted with the N-lithium salt. The 3-(4'-OP-1'-phenyl/4'-OP-1'-naphthyl)naphtho[1,8-de]-1,2-thiazine-1,1-dioxides may be prepared in a similar manner by reacting the Grignard or lithium reagent with 2,3-dihydro-3-oxo-naphtho[1,8-de]-1,2-thiazine-1,1-dioxide, its pseudo-chloride or the N-lithium derivative thereof.

The preparation of the 3-(4'-OP-1'-phenyl/4'-OP-1'-naphthyl)benz[d]isothiazole-1,1-dioxide starting materials is illustrated below.

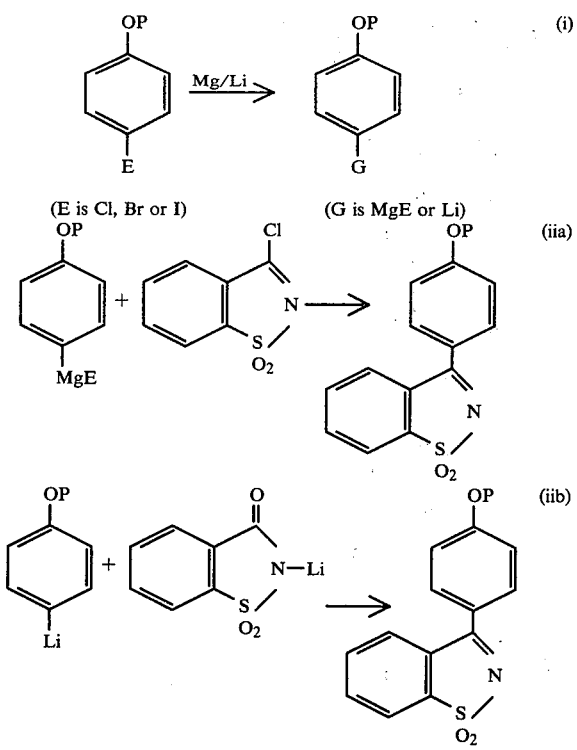

The groups selected for protecting the functional phenolic or naphtholic hydroxy group and other hydroxy groups that may be present in the phenol or 1-naphthol should be stable to and compatible with organolithium and Grignard reagents and should protect the hydroxy group(s) against reaction under the conditions encountered in the subject method and in the subsequent steps in the synthesis of the aforementioned N-acylated sulfam(na)phthalein products. In addition, the protecting group selected should be capable of being easily removed under weakly acid conditions to regenerate the hydroxy group(s) without the removal of or adversely affecting the N-substituent or other substituents that may be present. Alkyl groups, such as methyl and ethyl, may be employed in those instances where they can be removed without removal of the N-substituent. Because they can be readily removed without disturbing the N-substituent or other substituents, the phenol or 1-naphthol preferably is protected with methoxymethyl, 2'-tetrahydropyranyl or dimethyl-t-butylsilyl. The blocked phenols and 1-naphthols employing these protecting groups may be prepared by methoxymethylation as described, for example, by Kaoru Fuji et al, Synthesis, 4, pp. 276-277 (1975), by tetrahydropyranylation as described, for example, by William E. Parham et al, J. Amer. Chem. Soc., 70, pp. 4187-4189 (1948) or by silylating with dimethyl-t-butylsilyl chloride in the presence of imidazole as described by E. J. Corey et al, J. Amer. Chem. Soc., 94, pp. 6190-6191 (1972).

To prepare the 3-(4'-OP-1'-phenyl/4'-OP-1'-naphthyl)-3-(phenyl/naphthyl)-2,3-dihydrobenz[d]isothiazole-1,1-dioxides, the 3-(4'-OP-1'-phenyl/4'-OP-1'-naphthyl)benz[d]isothiazole-1,1-dioxide is reacted with an equimolar amount and generally, is reacted with an excess, of usually about 0.1 mole of a phenyllithium or a naphthyllithium reagent in an inert organic solvent, such as, benzene, diethyl ether, dioxane, hexane, toluene, petroleum ether or tetrahydrofuran. The reaction temperature may vary over a relatively wide range from about −80° to 50° C. as may be readily determined for the particular reagent. For achieving maximum yields, the reaction generally is conducted at a temperature below about 0° C. and preferably between about −65° C. and −25° C.

The phenyl- or naphthyllithium reagent ultimately forming the B moiety of the blocked intermediates and the ultimate sulfam(na)phthalein products may be substituted or unsubstituted and may be prepared from the corresponding halosubstituted compound. For example, N,N-dimethylaniline may be halogenated to give the 4-halo compound which, in turn, is reacted with lithium metal or n-butyllithium to yield the 4-lithium compound. Halogenation may be carried out in a conventional manner using either chlorine or bromine, with or without a catalyst, or using N-bromosuccinimide or iodinemonochloride. When lithium metal is employed in the preparation of the 4-lithium compound, the halo substituent may be chloro, bromo or iodo and is either bromo or iodo when a lithium exchange reaction is employed. If substituents, such as, hydroxy, are present, they should be blocked with the appropriate protecting group to render them compatible with organometallic reagents prior to conversion to the 4-lithium compound. The protecting groups, of course, should be removable under mildly acidic conditions so that the substituents on the aryl moiety forming the B moiety can be regenerated simultaneously with the regeneration of the functional -OH group of the phenolic or naphtholic moiety, i.e., the A moiety. As noted above, hydroxy groups in addition to the functional -OH of the phenol or 1-naphthol may be blocked simultaneously with the functional hydroxy group, for example, by tetrahydropyranylation or methoxymethylation. Groups other than hydroxy that should be protected may be blocked prior to or subsequent to the blocking of the functional -OH. For example, carboxy group(s) may be protected by reacting a carboxy-substituted 4-halophenol (or 4-halo-1-naphthol) with 2-amino-2-methyl-1-propanol followed by blocking of the functional -OH. Sulfonamido (-NH-SO₂-R°) and sulfamoyl (-SO₂-NH-R°) substituents may be protected by a t-butyl group.

As mentioned previously, the compounds provided by the subject method are useful as starting materials in the method disclosed and claimed in aforementioned copending application Ser. No. 836,010. As discussed therein, the 3-(4'-OP-1'-phenyl/4'-OP-1'-naphthyl)-3-(phenyl/naphthyl)-2,3-dihydrobenz[d]isothiazole-1,1-dioxides prepared as described above are reacted with a carboxylic acid halide in pyridine solution to give the corresponding N-acylated compound. About 1 to 2 moles of acid halide are used for each mole of the isothiazole-1,1-dioxide. Since the reaction is exothermic, external heating may not be necessary, but the reaction mixture may be heated to facilitate completion of the reaction, if desired. Ordinarily, the reaction temperature ranges between about 0° and 100° C., and preferably, the reaction is conducted in an inert atmosphere, for example, under nitrogen.

Optionally, the acylation step may be carried out by first reacting the isothiazole-1,1-dioxide with an equimolar amount or slight excess (∼0.1 M) of an alkali metal hydride, MH, wherein M is sodium, potassium or lithium in an inert organic solvent at about 0° to 100° C., preferably in an inert atmosphere, and then reacting the N-alkali metal salt thus formed with the carboxylic acid halide. Usually the acid halide is added to the reaction mixture containing the N-alkali metal salt. However, the N-alkali metal salt may be isolated prior to reaction with the acid halide, if desired. Solvents suitable for use in the alternate method of forming the N-acylated compound include dioxane, tetrahydrofuran, ethylether and benzene. The alkali metal, like the pyridine, affords substitution of the ring nitrogen of the isothiazole moiety in the acylation reaction.

Carboxylic acid halides are well known and may be prepared in a conventional manner, for example, by reacting the selected carboxylic acid, RCOOH, with phosphorus trichloride, phosphorus pentachloride or thionyl chloride to give the corresponding RCOCl, or by reacting the selected ROH with phosgene to give the corresponding ClCOOR.

Subsequent to the acylation step, the protecting group P is removed from the functional -OH by treating with acid having a pH between about 0.1 and 5.0 at a temperature between about 20° and 100° C. The acid may be an inorganic acid, such as, hydrochloric acid or sulfuric acid in a protic solvent, e.g., water, alkanol, such as, methanol or ethanol, or aqueous alkanol, or the acid may be an organic acid, such as, acetic acid or trifluoroacetic acid alone or in a protic solvent, such as those mentioned above. As indicated previously, any other protecting groups that may be present are removed simultaneously with the protecting group on the functional -OH.

The following examples are given to further illustrate the present invention and are not intended to limit the scope thereof.

EXAMPLE 1

Preparation of the compound having the formula:

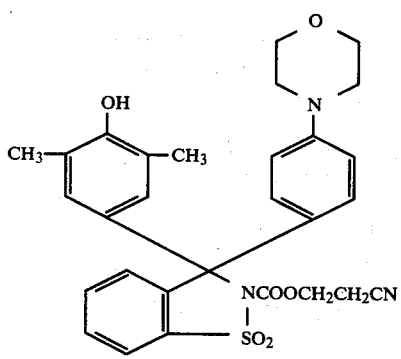

(a) N-(p-bromophenyl)morpholine (0.4 g.) was added to 20 ml. of tetrahydrofuran (THF) and the solution cooled to −65° C. To the solution was added 0.69 ml. of 2.4 M butyllithium in hexane with stirring and stirring was continued for 1 hour. (After 15 minutes the solution became cloudy and a white precipitate formed.) To this solution was added 0.5 g. of 3-(3',5'-dimethyl-4'-methoxymethoxy-1'-phenyl)benz[d]-isothiazole-1,1-dioxide in 2 ml. THF at −65° C. under nitrogen. The resulting reaction mixture was a clear orange-yellow solution. The reaction mixture was stirred for 1 hour, poured into 100 ml. of water, made acidic with conc. hydrochloric acid (pH 6), and extracted with ether. The ether was dried over Na₂SO₄ and evaporated leaving an oil. The oil was taken up in ligroin (boiling range 30°–60° C.) and refluxed for 1 hour. The white solid that formed was collected to give 0.7 g. of 3-(3',5'-dimethyl-4'-methoxymethoxy-1'-phenyl)-3-(4''-N-morpholinyl-1''-phenyl)-2,3-dihydrobenz[d]-isothiazole-1,1-dioxide having the formula:

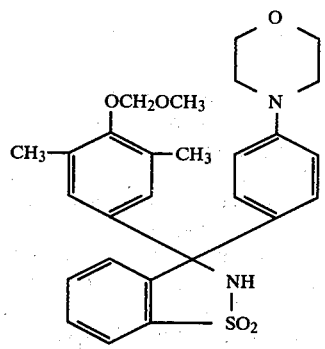

(b) The compound prepared in steps (a) (0.7 g.) was placed in 20 ml. of pyridine under nitrogen and 0.15 ml. of β-cyanoethylchloroformate (ClCO₂CH₂CH₂CN) was added to the pyridine solution. The resulting reaction solution was stirred 1 hour, warmed gently and then poured into 100 ml. of water and extracted with chloroform. The chloroform was dried over Na₂SO₄, evaporated and the solid that formed was extracted with ligroin (boiling range 30°–60° C.). The solid obtained was the N-acylated compound, 3-(3',5'-dimethyl-4'-methoxymethoxy-1'-phenyl)-3-(4''-N-morpholinyl-1''-phenyl)-2-(β-cyanocarbethoxy)-2,3-dihydrobenz[d]isothiazole-1,1-dioxide having the formula:

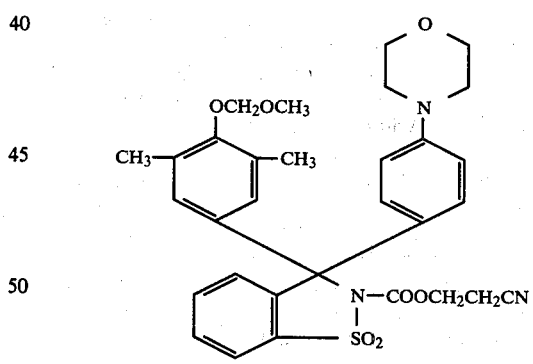

(c) The compound obtained in step (b) was then dissolved in methanol, made acidic with conc. hydrochloric acid and refluxed 1 hour. TLC from ether on silica gel showed 4 spots. The methanol solution was evaporated to leave 0.6 g. of solid. 200 mg. of solid in ether was placed on silica gel PQ1-1000 plates and the dark band was removed with acetone after drying. The acetone was removed, ether added and the white solid that formed was recovered by filtration to give the title compound.

The 3-(3',5'-dimethyl-4'-methoxymethoxy-1'-phenyl)-benz[d]isothiazole-1,1-dioxide having the formula:

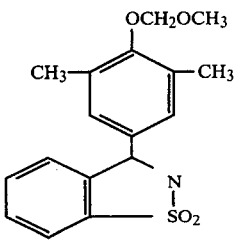

used in step (a) above was prepared as follows:

(i) Into a 2 liter three neck flask, fitted with a mechanical stirrer, nitrogen inlet and a dropping funnel, was placed 700 ml. of dry chloroform. The flask was immersed in an ice-water bath. Powdered phosphorus pentoxide (300.0 g.) was added to the vigorously stirred, cold chloroform. To this mixture was added over a 1 hour period a solution of 4-bromo-2,6-dimethylphenol (201.0 g.) in 400 ml. of dry dimethoxymethane. During this time the phosphorus pentoxide powder fused into an amorphous mass and stirring became difficult. TLC analysis (9:1 petroleum ether-ethyl acetate on silica gel) indicated that much unreacted starting phenol was still present. The temperature of the reaction mixture was allowed to rise to about 25° C. Additional 50 g. increments of phosphorus pentoxide were added to the stirred reaction mixture every 30–45 minutes until TLC analysis indicated the absence of starting phenol. The organic layer was decanted, washed with two 250 ml. portions of aqueous 10% sodium hydroxide and dried over calcium sulfate. The solvent was removed under reduced pressure leaving a pale yellow oil which was distilled from 25 g. of anhydrous potassium carbonate to give 220.0 g. of 4-bromo-2,6-dimethylmethylenemethoxyphenyl ether as a colorless oil (boiling point 112° C. and 0.5 mm Hg).

(ii) 4-Bromo-2,6-dimethyl-methylenemethoxyphenyl ether (85.04 g.; 0.347 mole) was dissolved in approximately 800 ml. of tetrahydrofuran. The solution was cooled to −75° C. under a nitrogen blanket, and 2.4 M n-butyllithium in hexane (144.8 ml; 0.346 mole) was added dropwise. Addition was completed within a 2 hour period giving a white slurry.

(iii) Saccharin (61.2 g; 0.334 mole) was dissolved in 600 ml. of dry tetrahydrofuran, and the solution was cooled to approximately −75° C. 2.4 M n-butyllithium in hexane (130.4 ml; 0.311 mole) was slowly added dropwise to the cooled solution under a nitrogen blanket. The temperature was not allowed to rise above −70° C. Addition was completed in about 90 minutes, giving a clear, very pale yellow solution.

(iv) The yellow solution obtained in step (iii) was slowly added (over a 3 hour period) to the white slurry obtained in step (ii) while keeping the temperature at −70° C. During this time the solids disappear giving a clear, caramel colored reaction mixture that first tends to darken with time and then gradually lightens. The reaction mixture was allowed to come to room temperature overnight and then was treated with 36.0 g. of ammonium chloride in 250 ml. of water, while cooling in an ice-water bath. The organic portion was decanted and dried over anhydrous calcium sulfate. The solvent was removed under reduced pressure to give a pink colored oil that became solid on standing in open air. The solid was recrystallized twice from 1-propanol, washed with a 60:40% mixture of petroleum ether-tetrahydrofuran and dried under vacuum to give 68.0 g. of the title compound as a white, crystalline solid.

3-(3',5'-dimethyl-4'-methoxymethoxy-1'-phenyl)-benz[d]isothiazole-1,1-dioxide also was prepared as follows:

Dry tetrahydrofuran (10–15 ml.) was added to magnesium turnings (0.20 g.) under nitrogen. A solution of 4-bromo-2,6-dimethyl-methylenemethoxyphenyl ether (2.0 g.) in tetrahydrofuran (30 ml.) was added gradually to the magnesium turnings with stirring and heating. After about twenty minutes of external heating to reflux, a self-sustaining reaction was observed. The remaining solution of phenyl ether was then added at a rate to maintain a comfortable reaction. Refluxing with external heating was continued after addition was complete and after one hour, the solution was cooled to room temperature and held under nitrogen. A solution of saccharin pseudochloride (1.89 g.) in tetrahydrofuran (40 ml.) was cooled to −78° C. and the previously prepared solution of magnesium bromide reagent was added dropwise to the pseudo-chloride solution under nitrogen. The resulting reaction mixture was stirred cold for about 2 hours and then stirred at room temperature overnight. The reaction mixture was then cooled in an ice water bath and treated with saturated aqueous ammonium chloride solution. The aqueous solution was extracted with chloroform several times and the combined chloroform extracts washed with water and dried over anhydrous sodium sulfate followed by drying over anhydrous calcium sulfate. Upon removing the chloroform, a colorless oil was obtained which was extracted several times with small portions of light petroleum ether to leave behind a pale yellow tacky tar. The yellow tar was treated with ether leaving behind an off-white solid. The off-white solid was dissolved in a small amount of chloroform, treated with carbon black and filtered through Celite. Upon removing the solvent, the title compound was obtained as an off-white solid which was dried under vacuum in the presence of $P_2O_5$. Yield 0.520 g.

3-chlorobenz[d]isothiazole-1,1-dioxide (saccharin pseudo-chloride) was prepared as follows:

35 g. of saccharin and 43.7 g. of $PCl_5$ were heated at 170° C. for 1178 hours during which time complete solution occurred and $POCl_3$ began to reflux. The $POCL_3$ was removed at reduced pressure to leave a crystalline residue. Diethyl ether was added to the crystalline residue and stirred well. The title compound was recovered as white crystals, 12.5 g. (melting range 146°–147° C.).

The N-(p-bromophenyl)morpholine having the formula

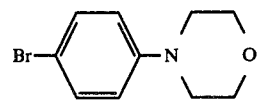

used in step (a) above was prepared as follows:

25 g. of N-phenylmorpholine was dissolved in 200 ml. of carbon tetrachloride and stirred well. To this was added all at once 27.2 g. of N-bromosuccinimide. There was an exotherm to 45° C. The reaction solution was stirred until the temperature began to decrease and then was heated to reflux for 3 hours. TLC on silica gel with 3/2 petroleum ether/ether indicated that the reaction was complete. The reaction solution was then cooled, the succinimide removed by filtration and the solution evaporated to yield a yellow solid. The solid was dissolved in 250 ml. of ethanol and cooled to give 22 g. of the title compound as white crystals.

The β-cyanoethylchloroformate having the formula (CNCH$_2$CH$_2$COOCl) used in step (b) above was prepared as follows:

To 100 ml. of dry benzene, cooled in an ice bath, was added phosgene gas until 34.0 g. was collected. Hydroxyacrylonitrile (20.2 g.) was added to the cooled phosgene solution. (The temperature rose slightly to approximately 8° C.). The resulting heterogeneous mixture was cooled to 3° C. with stirring, and pyridine (22.6 g.) in 25 mls. of benzene was added dropwise. Heat was evolved, and the temperature was not allowed to rise above 10° C. Very vigorous stirring was maintained until solid began to form. After about 1 hour, the reaction mixture was stirred at approximately 5° C. for 15 minutes, then allowed to come to 15° C.–20° C. and stirred for another 15 minutes. The reaction mixture was then cooled to 5° C. and 26 ml. of ice water was added in increments. The solids dissolved with liberation of heat and evolution of gas. The temperature was not allowed to rise above 15° C. over the next 15–20 minutes. The reaction mixture was then stirred at room temperature for 2 hours, the benzene layer decanted and dried over anhydrous Na$_2$SO$_4$, followed by drying over anhydrous CaSO$_4$. The solvent was removed under reduced pressure to yield an almost colorless oil which was redistilled under vacuum at a boiling range of 68.5°–70.5° C. (pot temperature 98°–103° C.) to yield 18.2 g. of the title compound as a colorless oil.

EXAMPLES 2 AND 3

The compounds having the formulas

Example 2

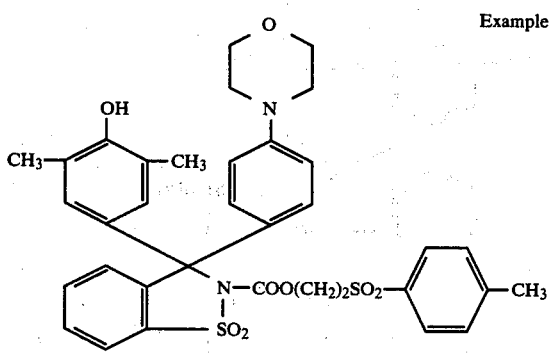

Example 3

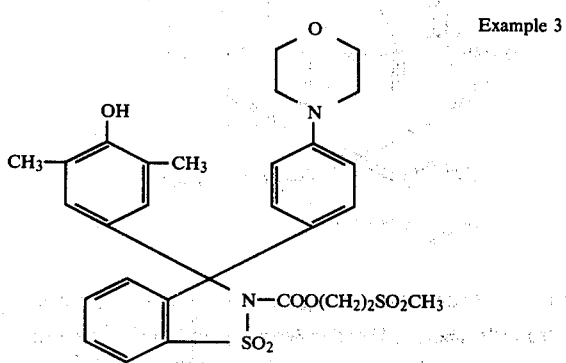

were prepared in the same manner described in Example 1 except that the 3-(3',5'-dimethyl-4'-methoxymethoxy-1'-phenyl)-3-(4''-N-morpholinyl-1''-phenyl)2,3-dihydrobenz[d]isothiazole-1,1-dioxide was reacted in step (b) with the appropriate acylating agents, namely,

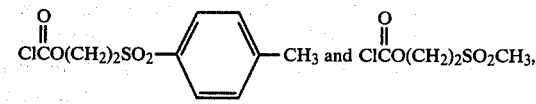

to yield the corresponding N-acylated compounds which were treated as in step (c) above to remove the protecting groups.

EXAMPLES 4 AND 5

The compounds having the formulas

Example 4

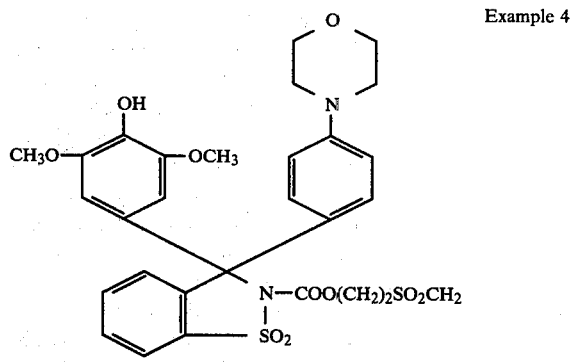

Example 5

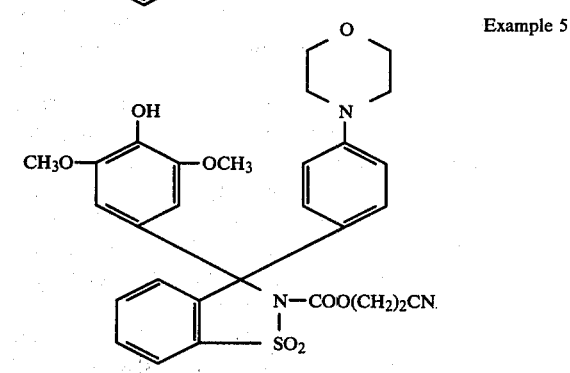

were prepared according to the procedure described in Example 1 except that 3-(3',5'-dimethoxy-4'-methoxymethoxy-1'-phenyl)-benz[d]isothiazole-1,1-dioxide was used in the reaction of step (a) and the appropriate acylating agents, namely,

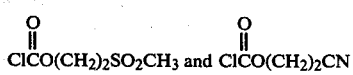

were used in step (b).

The 3-(3',5'-dimethoxy-4'-methoxymethoxy-1'-phenyl)-benz[d]isothiazole-1,1-dioxide used in step (a) above was prepared as follows:

(i) Using an 18 gauge needle-syringe, 20.0 mls. of n-butyllithium (2.4 M in hexane) was added dropwise over 1 hour to a solution of 9.16 g. of saccharin (previously dried overnight at 80° C. in vacuo) in 250 mls. of dry tetrahydrofuran under nitrogen at −75° C. to −73° C. with rapid stirring. The reaction solution comprising the N-lithium salt of saccharin in tetrahydrofuran was used directly in step (iii) without isolating the lithium salt.

(ii) In a dried 1 l. flask, 13.86 g. of 4-bromo-2,6-dimethoxy-methylenemethoxyphenyl ether was dissolved in 300 mls. of dry tetrahydrofuran under nitrogen, and 20.83 mls. of n-butyllithium (2.4 M in hexane) was added dropwise with stirring at −75° C. After addition was complete, the reaction solution was stirred at −75° C. for about 30 minutes.

(iii) The solution of saccharin lithium salt prepared in step (i) was transferred to an addition funnel using a double-tip needle under nitrogen pressure and added to the solution of 4-Li-2,6-dimethoxy-methylenemethoxyphenyl ether prepared in step (ii) over about 15 minutes with stirring at a temperature of −75° C. to −70° C. The reaction mixture was stirred for about 2 hours at −75° C. and then warmed to 0° C. during an hour.

(iv) A solution of 5.2 g. of ammonium chloride in 175 mls. of water was added dropwise to the reaction mixture of step (iii) and the reaction mixture was transferred to a 1 l. separatory funnel. After the two phases separated, the aqueous phase was removed and the pH was lowered from about 11 to about 6–7 by the dropwise addition of aqueous 5% hydrochloric acid solution. (A color change from yellow to colorless was observed.) The aqueous phase was returned to the separatory funnel, partitioned and the aqueous phase again separated and then extracted with fresh ether (100 mls.). The ether and tetrahydrofuran/hexane extracts were combined, dried over magnesium sulfate overnight, filtered and the solvent removed to leave a yellow oil which crystallized. Ether (100 mls.) was added to the crystalline material and the crystalline material was ground under ether in a mortar, filtered, washed with more ether followed by petroleum ether and air dried. A second crop was collected from the filtrate to give a total yield of 13.0 g. of the title compound.

The methoxymethylation of 4-bromo-2,6-dimethoxyphenol was carried out as follows:

To a 3 liter flask was added 300 g. of P₂O₅ under nitrogen and 800 ml. of chloroform (previously dried over P₂O₅). The mixture was cooled to −15° C. with a dry-ice acetone bath and then 50 g. of 4-bromo-2,6-dimethoxyphenol in 800 ml. of dimethoxymethane was added over a 25 minute period while maintaining the temperature at −15° C. or below. To the resulting reaction mixture was added 1 ml. of conc. sulfuric acid and then the temperature was allowed to come to room temperature. During this time, a tacky mass of P₂O₅ developed. The reaction mixture was stirred for 3 hours. TLC on silica gel with 3/2 petroleum ether/ether indicated that the reaction was complete. The chloroform was then decanted into 400 ml. of 10% aqueous sodium hydroxide, stirred well and the chloroform layer separated, washed with water, dried over Na₂SO₄ and evaporated to leave light tan crystals. n-Propanol was added to the crystalline residue, stirred and filtered to give 32.7 g. of the title compound as white crystals (melting range 98°–100° C.).

EXAMPLES 6–10

The compounds having the formulas:

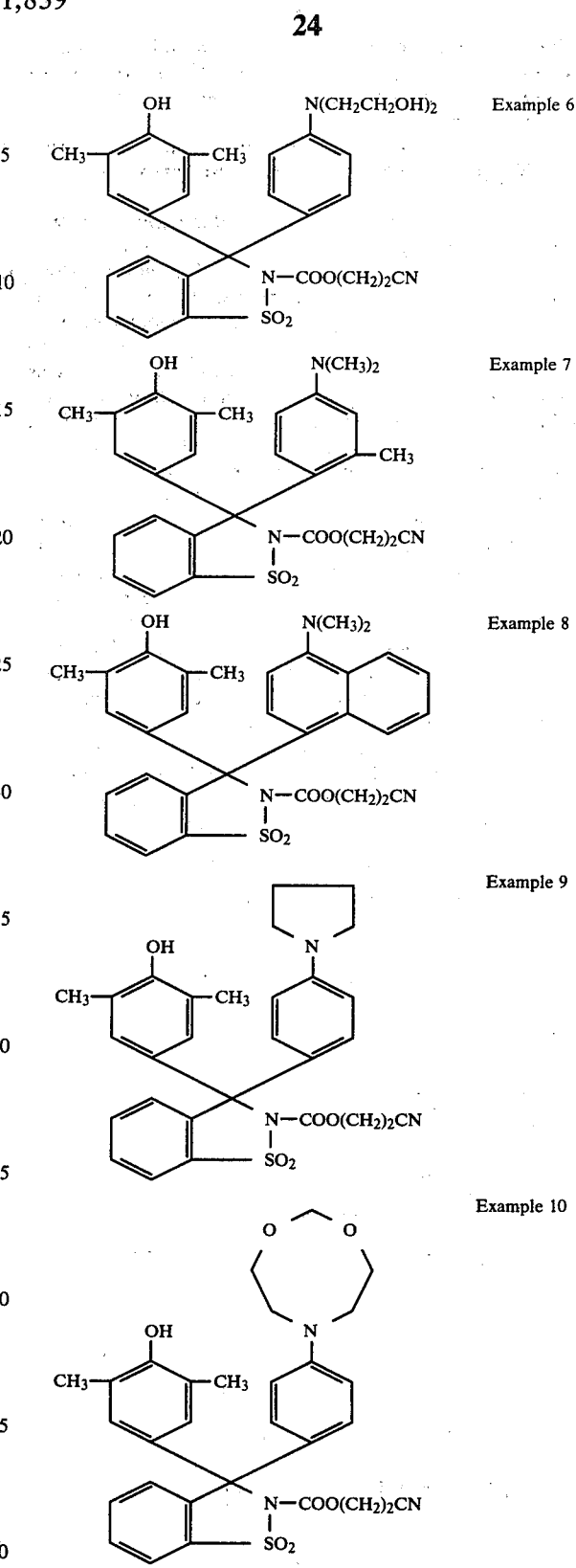

were prepared according to the procedure given in Example 1 except that in step (a) the 3-(3′,5′-dimethyl-4′-methoxymethoxy-1′-phenyl)benz[d]isothiazole-1,1-dioxide was reacted with the appropriate lithium reagent, namely.

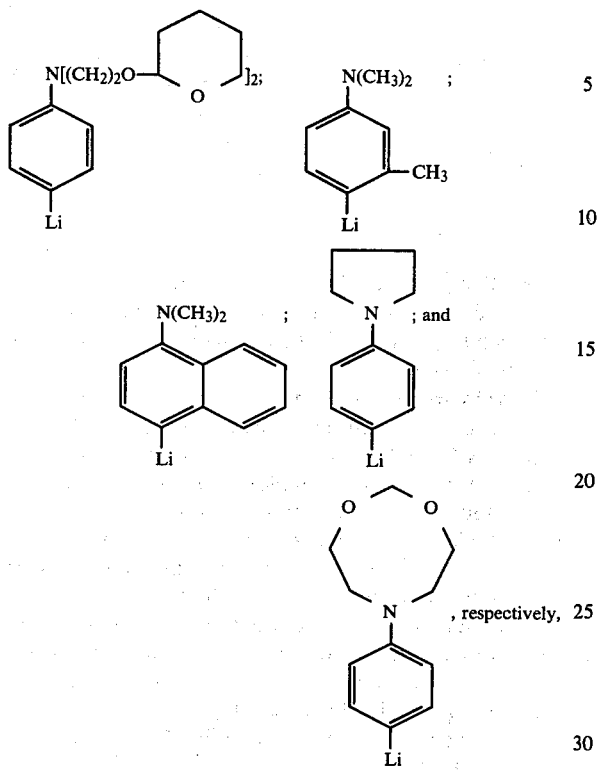

, respectively, and the 2'-tetrahydropyranyl groups were removed from the protected N,N-di(β-hydroxyethyl)anilino moiety of Example 7 in step (c) simultaneously with the 4'-methoxymethyl protecting group.

N-(p-Li-phenyl)tetrahydro-2H,4H-1,3,6-dioxazocine may be prepared by reacting the corresponding p-halophenyl compound with n-butyllithium. The N-(p-halophenyl)tetrahydro-2H,4H-1,3,6-dioxazocines are prepared by reacting p-halo-N,N'-di(β-hydroxyethyl)aniline with certain dihalomethanes in the presence of a solid alkali metal hydroxide or concentrated aqueous solution thereof and a quaternary ammonium salt. These compounds and their preparation form the subject matter of U.S. Patent Application Ser. No. 836,066 of Louis Cincotta, James W. Foley and Marcis M. Kampe filed concurrently herewith.

EXAMPLE 11

Preparation of the compound having the formula:

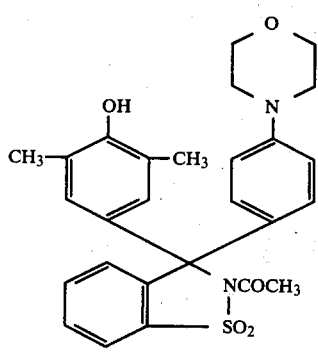

(a) N-(p-bromophenyl)morpholine (0.4 g.) was added to 20 ml. of tetrahydrofuran (THF) and the solution cooled to −65° C. To the solution was added 0.69 ml. of 2.4 M butyllithium in hexane with stirring and stirring was continued for 1 hour. (After 15 minutes the solution became cloudy and a white precipitate formed.) To this solution was added 0.5 g. of 3-(3',5'-dimethyl-4'-methoxymethoxy-1'-phenyl)benz[d]-isothiazole-1,1-dioxide in 2 ml. THF at −65° C. under nitrogen. The resulting reaction mixture was a clear orange-yellow solution. The reaction mixture was stirred for 1 hour, poured into 100 ml. of water, made acidic with conc. hydrochloric acid (pH 6), and extracted with ether. The ether was dried over Na₂SO₄ and evaporated leaving an oil. The oil was taken up in ligroin (boiling range 30°-60° C.) and refluxed for 1 hour. The white solid that formed was collected to give 0.7 g. of 3-(3',5'-dimethyl-4'-methoxymethoxy-1'-phenyl)-3-(4''-N-morpholinyl-1''-phenyl-2,3-dihydrobenz[d]-isothiazole-1,1-dioxide having the formula:

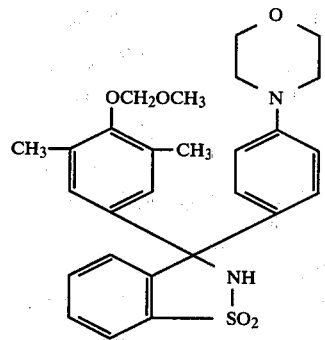

(b) The compound prepared in step (a) (0.7 g.) was dissolved in 15 ml. of pyridine under nitrogen and 0.11 ml. of

was added to the pyridine solution. A white precipitate formed. The resulting reaction solution was stirred and warmed gently (total stirring time 1 hour) and then poured into 100 ml. of water and extracted with chloroform. The chloroform was dried over anhydrous Na₂SO₄ and evaporated leaving a solid. The solid obtained was the N-acylated compound, 3-(3',5'-dimethyl-4'-methoxymethoxy-1'-phenyl)-3-(4''-N-morpholinyl-1''-phenyl)-2-(acetyl)-2,3-dihydrobenz[d]isothiazole-1,1-dioxide having the formula:

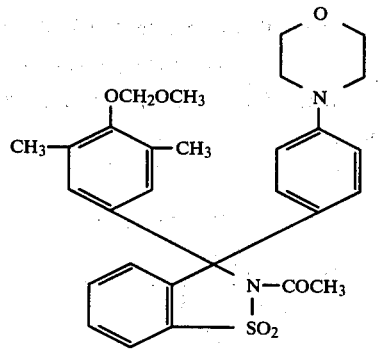

(c) The compound obtained in step (b) was then dissolved in 25 ml. of methanol, made acidic with conc. hydrochloric acid and refluxed 2 hours. The solution was evaporated leaving a tan solid. TLC of a sample on silica gel PQ1-1000 with ether gave a dark band on drying. The dark band was removed, washed with acetone and the acetone removed after filtering to yield a gum. Ether was added to the gum and the resulting solution refluxed to give a white solid that was isolated to give the title compound.

EXAMPLES 12–14

The compounds having the formulae

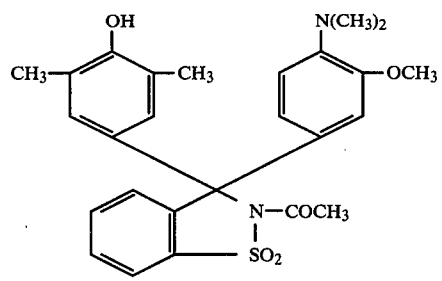
Example 12

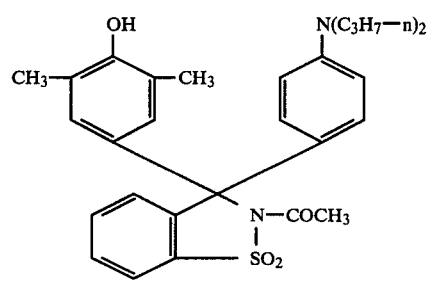
Example 13

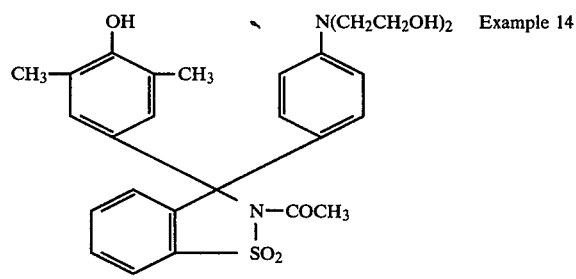
Example 14 were prepared according to the procedure given in Example 11 except that in step (a) the 3-(3',5'-dimethyl-4'-methoxymethoxy-1'-phenyl)benz[d]isothiazole-1,1-dioxide was reacted with the appropriate lithium reagent, namely,

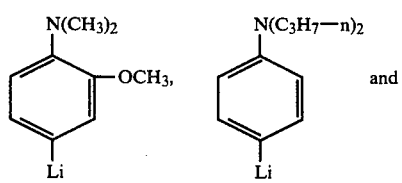
and

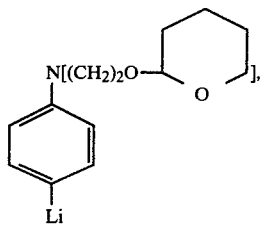

respectively, and the 2'-tetrahydropyranyl groups were removed from the -N,N-di(β-hydroxyethyl)anilino moiety simultaneously with the methoxymethyl protecting group in step (c).

Tetrahydropyranylation of p-Br-N,N-di(β-hydroxyethyl)-aniline was carried out as follows:

p-Br-N,N-di(β-hydroxyethyl)aniline (20.0 g.) was dissolved in 475 ml. of dichloromethane containing 60 ml. of dihydropyran. To this solution was added 1 ml. of conc. HCl, and the reaction solution was stirred for about 5.5 hours. The solution was then washed with water containing enough sodium hydroxide to neutralize any acid present. The dichloromethane was separated, dried over anhydrous sodium sulfate and evaporated under reduced pressure with a steam bath (aspirator) leaving an oil. The oil was heated to 115° C. at 0.1 mm Hg to distill off impurities leaving 33.0 g. of the title compound.

The corresponding 4-Li compound was prepared by dissolving 4-bromo-N,N-di(β-2'-tetrahydropyranyloxyethyl)aniline (10.0 g.) in 100 ml. of tetrahydrofuran, cooling the solution to −65° C. and adding 10 ml. of n-butyllithium (2.4 M in hexane) under nitrogen at a rate to maintain the temperature at −65° C.

EXAMPLES 15 AND 16

The compounds having the formulae

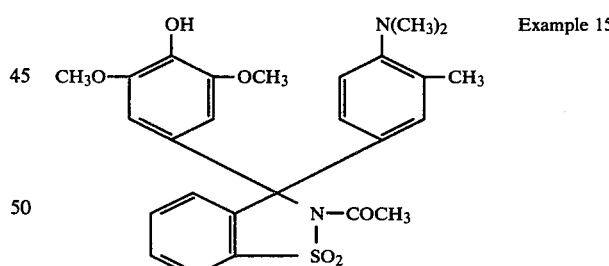
Example 15

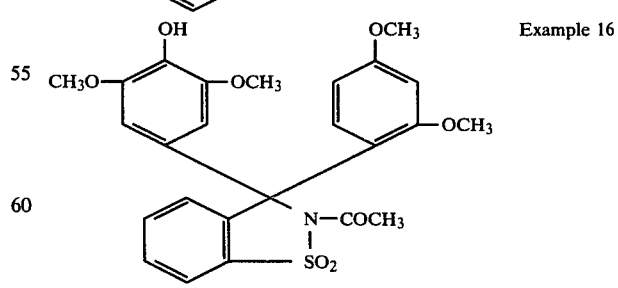
Example 16 were prepared according to the procedure given in Example 11 except that 3-(3',5'-dimethoxy-4'-methoxymethoxy-1'-phenyl)-benz[d]isothiazole-1,1-dioxide was reacted with the appropriate lithium reagent, viz.,

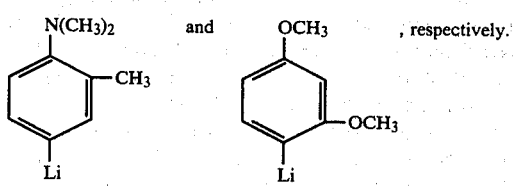, respectively.

EXAMPLES 17–23

The compounds having the formulae

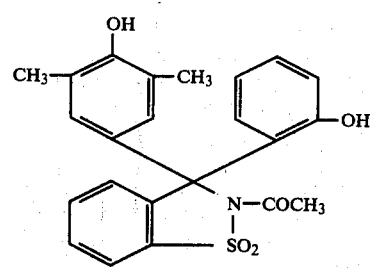 Example 17

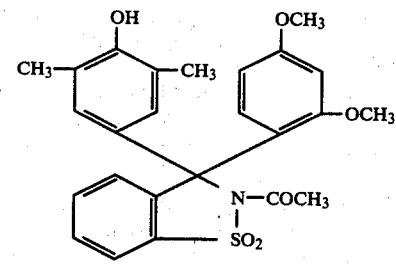 Example 18

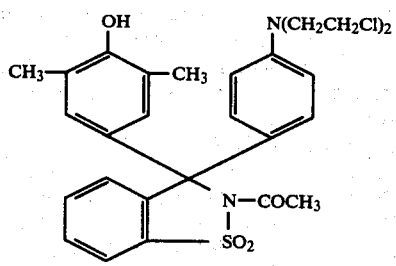 Example 19

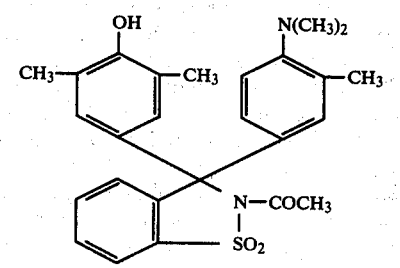 Example 20

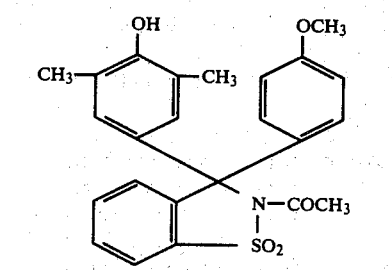 Example 21

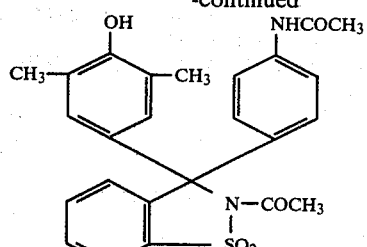 Example 22

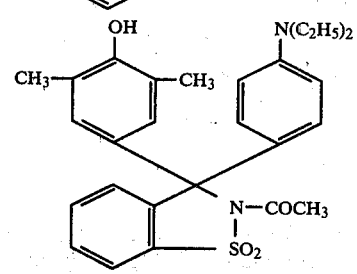 Example 23 were prepared by reacting 3-(3′,5′-dimethyl-4′-methoxymethoxy-1′-phenyl)benz[d]isothiazole-1,1-dioxide with the selected aryl lithium reagent as described in step (a) of Example 11 above to give the corresponding 3,3-disubstituted-2,3-dihydrobenz[d]isothiazole-1,1-dioxide. The lithium reagents employed were

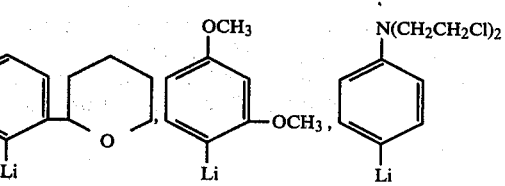

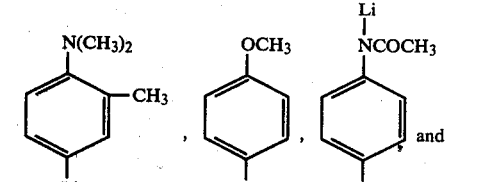, respectively.

The 3,3-disubstituted-2,3-dihydrobenz[d]isothiazole-1,1-dioxides obtained were then sequentially reacted in dioxane at room temperature with NaH (as 57% oil dispersion) and

ClCCH₃ by adding the acetyl chloride to the dioxane solution of the N-sodium salt to give the corresponding

N—CCH₃ intermediates. The intermediates were then treated with dilute hydrochloric acid to remove the protecting group(s) to give the title compounds.

The optional acylation step is illustrated as follows:

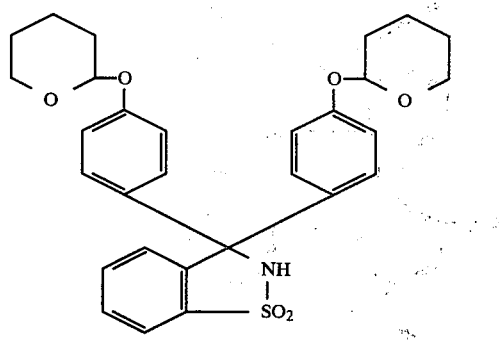

A

Compound A having the above formula (10.0 g.) was placed in 100 ml. of dioxane and 0.88 g. of sodium hydride (as 57% oil dispersion) was added at room temperature under nitrogen (hydrogen evolution was observed). The resultant mixture comprising the N-sodium salt of the above compound was stirred 1 hour and then 2.4 ml. of ClCOOCH$_2$CH$_2$CN was added. A white precipitate formed immediately. The reaction mixture was stirred overnight, then poured into 200 ml. water. The aqueous mixture was extracted with three 250 ml. portions of ether, which were combined and dried over sodium sulfate. The ether was removed in vacuo and the resulting solid washed with petroleum ether. Upon drying, 10.5 g. of the crude N-acylated derivative was obtained. The N-acylated compound has the formula

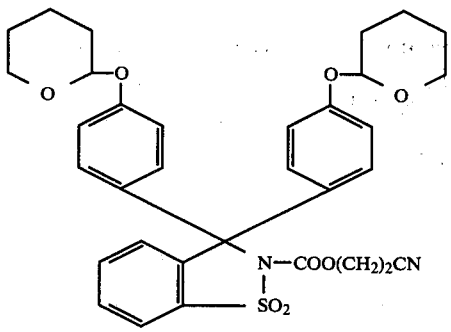

B

The intermediate having the formula

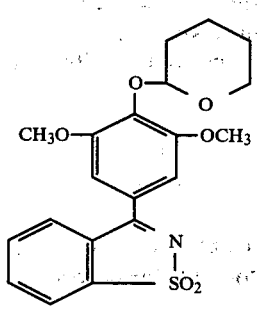

was prepared as follows:

(i) Saccharin (8.79 g.) previously dried in vacuo over P$_2$O$_5$ was dissolved in 240 ml. of dry tetrahydrofuran in a flame-dried 500 ml. flask, and the solution was then cooled to −75° C. in a dry ice-acetone bath under nitrogen. n-Butyllithium (18.8 ml.; 2.4 M in hexane) was added dropwise to the saccharin solution over 40 minutes with stirring while maintaining the temperature between about −75° C. and −70° C.

(ii) 2'-Tetrahydropyranyl 4-bromo-2,6-dimethoxyphenyl ether (15.23 g.) previously dried in vacuo over P$_2$O$_5$ was dissolved in 120 ml. of dry tetrahydrofuran in a second flame-dried 500 ml. flask, and the solution was cooled to −75° C. n-Butyllithium (20 ml.; 2.4 M in hexane) was added to the ether solution while maintaining the temperature between about −75° C. and −70° C. After addition was complete, stirring was continued at −75° C. for 30 minutes.

(iii) The solution of the N-lithium salt of saccharin in tetrahydrofuran prepared in step (i) was added to the solution prepared in step (ii) under nitrogen using a double-tipped needle over a period of 15 minutes. During addition the temperature was kept below −70° C. The reaction mixture was stirred at −75° C. for 2 and ¾ hours and then allowed to warm to −10° C.

(iv) A solution of ammonium chloride (5.35 g.) dissolved in 50 ml. of water was added dropwise to the reaction mixture. The pH was lowered to about 8 with cold aqueous 5% HCl, and the mixture was diluted to a total volume of 900 ml. The tetrahydrofuran-hexane phase (250 ml.) was separated, dried over anhydrous sodium sulfate, filtered and stripped to dryness leaving a yellow oil. The pH of the aqueous phase was lowered to about 6 with aqueous 5% HCl and extracted with 200 ml. of ether. The ether extract was dried over anhydrous sodium sulfate, filtered and combined with the yellow oil obtained from drying the organic phase. A white precipitate formed in a yellow solution. The precipitate was filtered, washed with ether and air-dried to give 8.34 g. of solids which were taken up in 100 ml. of boiling methanol. The methanol solution was cooled in an ice bath, and the precipitate that formed was filtered, washed with methanol-ether to give the title compound as a yellow powder.

The 2'-tetrahydropyranyl 4-bromo-2,6-dimethoxyphenyl ether used above was prepared as follows:

4-Bromo-2,6-dimethoxyphenol (59.0 g.) was dissolved in 280 ml. of dihydrofuran (98%) at room temperature. The solution was cooled to 3° C. in an ice-water bath, and five drops of phosphorus oxychloride was added with stirring. After storing the reaction mixture in a refrigerator overnight, white crystals were collected on a filter, washed thoroughly with n-pentane with grinding and isolated to give 56.5 g. of the title compound. A sample of the compound was recrystallized by dissolving in 25 ml. of warm chloroform, filtering (warm) and slowly adding 100 ml. of n-pentane. The solution was allowed to stand at room temperature for 10–15 minutes, scratched to induce crystallization and cooled in a refrigerator for 2 hours. The title compound was recovered by filtration, washed n-pentane and air-dried (melting range 122°–123° C.).

2'-Tetrahydropyranyl 4-bromophenyl ether was prepared as follows:

To 10.5 ml. of dihydropyran containing 2 drops of conc. HCl was added 10 g. of p-bromophenol. (The reaction was exothermic and the temperature rose to 35° C.) After addition was complete, the reaction solution was heated to 50° C. and then allowed to cool for 1 hour with stirring. 20 ml. of ether was added and 10 ml. of 10% aqueous sodium hydroxide solution was added to remove acid and any remaining p-bromophenol. The ether layer was dried over anhydrous sodium sulfate and evaporated under reduced pressure to leave an oil. 80 ml. of ethanol was added and the solution was allowed to stand. The white crystals that formed were recovered by filtration and vacuum dried (7.3 g., melting range 59°–60° C.). The mother liquor was reduced to one-half its original volume and cooled. The additional crystals that formed were recovered by filtration and dried to give 2.1 g. or a total yield of 9.4 g. of 2'-tetrahydropyranyl 4-bromophenyl ether.

The methoxymethyl ethers of 4-bromophenol and of 4-bromo-1-naphthol were prepared according to the procedures described in the above examples. The 2'-tetrahydropyranyl ethers of 4-bromo-2,6-diisopropylphenol and of 4-bromo-1-naphthol also were prepared according to the procedures described in the above examples.

The dimethyl-t-butylsilyl ether of 4-bromo-1-naphthol was prepared as follows:

4-Bromo-1-naphthol (22.1 g.) and dimethyl-t-butylsilyl chloride (18.1 g.) were dissolved in 50 ml. of dimethylformamide at room temperature. The resulting solution was cooled in an ice bath and imidazole (17.0 g.) added under nitrogen. (A slight exotherm was observed.) A solid precipitated and the reaction mixture was stirred overnight.

A small sample of the crude product was treated with water adjusted to a pH of about 4–5 with dilute HCl and the solids isolated and dried. TLC on silica gel using hexane showed the product but no starting material.

The reaction mixture remaining was poured into 1500 ml. of water at about 20° C. with stirring. The pH was adjusted to 4–5 with dilute HCl, and the solids were filtered, washed with water, and air dried for 2 hours and dissolved in 150 ml. of boiling isopropanol. The isopropanol solution was filtered while hot and then cooled slowly to room temperature. Crystals began to form and after standing at room temperature overnight, the solution was cooled in an ice water bath for 1 hour and filtered. The solid collected was washed with small amounts of isopropanol, air dried briefly and then dried in vacuo for 2 hours to give 24.3 g. of the title compound (melting range 70°–73° C.).

The methoxymethyl ether and the 2'-tetrahydropyranyl ether of 4-bromo-1-naphthol were converted to the corresponding 4-lithium derivatives by reaction with n-butyllithium according to the procedures described above.

It will be appreciated that the lithium derivatives of the blocked 1-naphthols may be reacted with the N-lithium salt of saccharin to give the corresponding 3-(4'-OP-1'-naphthyl)-benz[d]isothiazole-1,1-dioxide which, in turn, may be reacted with the selected phenyllithium or naphthyllithium reagent to give the corresponding 3-(4'-OP-1'-naphthyl)-3-(phenyl/naphthyl)-2,3-dihydrobenz[d]isothiazole-1,1-dioxide.

Where it is desired to prepare sulfamnaphthaleins, 2,3-dihydro-3-oxo-naphtho[1,8-de]-1,2-thiazine-1,1-dioxide or its pseudo-chloride may be substituted for the saccharin reagents used in the foregoing Examples to give the corresponding sulfamnaphthalein intermediates and products. The pseudo-chloride may be prepared from the 3-oxo thiazine by reaction with PCl5 as described above for the preparation of saccharin pseudo-chloride.

As mentioned above, the compounds of the present invention are useful as intermediates in the synthesis of certain 3,3-disubstituted-2,3-dihydrobenz[d]isothiazole-1,1-dioxides possessing a carbonyl group in the 2-position. Such compounds possessing a 4'-hydroxyphenyl moiety as one of the 3,3 substituents and a phenyl/naphthyl or 4'-substituted phenyl/4'-substituted naphthyl moiety as the other of the 3,3 substituents form the subject matter of copending U.S. Patent Application Ser. No. 836,021 of Stanley M. Bloom, Alan L. Borror and James W. Foley filed concurrently herewith and of copending U.S. Pat. applications Ser. Nos. 835,998; 836,005; 836,009) of Alan L. Borror and James W. Foley also filed concurrently herewith. As discussed in the aforementioned applications, compounds may be selected for use as classical pH-sensitive dyes or as photographic optical filter agents and filter agent precursors depending upon the 2-substituent of the benz[d]isothiazole ring. The photographic use of certain of the compounds as photographic optical filter agents and filter agent precursors forms the subject matter of copending U.S. Pat. application Ser. No. (836,006) of Stanley M. Bloom, Alan L. Borror and James W. Foley filed concurrently herewith. The 2,3-dihydrobenz[d]isothiazole-1,1-dioxides possessing a 4'-hydroxynaphthyl moiety as one of the 3,3 substituents and a naphthyl or 4'-substituted naphthyl moiety as the other of the 3,3 substituents form the subject matter of copending U.S. Pat. application Ser. No. 836,067 of Alan L. Borror, Louis Cincotta, Ernest W. Ellis and James W. Foley filed concurrently herewith, and as described therein, compounds may be selected for use as classical pH-sensitive indicator dyes or as antihalo dyes in photography.

Since certain changes may be made in the above processes and products without departing from the scope of the invention herein involved, it is intended that all matter contained in the above description shall be interpreted as illustrative and not in a limiting sense.

What is claimed is:

1. The compound of the formula

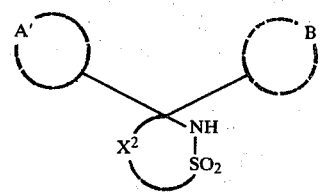

wherein A' is a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; B is a phenyl moiety, unsubstituted or substituted with one or more substituents compatible with organometallic reagents, the same or different, or a naphthyl moiety, unsubstituted or substituted with one or more substituents compatible with organometallic reagents, the same or different; P is a protecting group; and X² *represents the atoms necessary to complete a* 2,3-dihydrobenz-[d]isothiazole-1,1-dioxide moiety or a 2,3-dihydronaphtho-[1,8-de]-1,2-thiazine-1,1-dioxide moiety, said A' and B moieties being different.

2. A compound as defined in claim 1 wherein $X^2$ represents the atoms necessary to complete a 2,3-dihydrobenz-[d]isothiazole-1,1-dioxide.

3. A compound as defined in claim 1 wherein A' is a 4'-OP-1'-phenyl moiety.

4. A compound as defined in claim 1 wherein A' is a 4'-OP-1'-naphthyl moiety.

5. A compound as defined in claim 1 wherein B is a phenyl moiety.

6. A compound as defined in claim 1 wherein B is a naphthyl moiety.

7. A compound of the formula

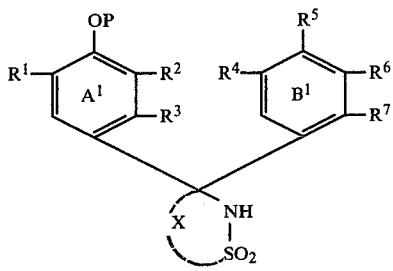

wherein P is a protecting group, $R^1$ and $R^2$ each are selected from hydrogen, alkyl, alkoxy, chloro and fluoro; $R^3$ is hydrogen, alkyl, alkoxy, or —OP; $R^2$ and $R^3$ taken together represent the carbon atoms necessary to complete a fused benzene ring; $R^4$ and $R^6$ each are selected from hydrogen, alkyl, alkoxy, chloro and fluoro; $R^5$ is hydrogen, alkyl, alkoxy, —$OP^I$ wherein $P^I$ is a protecting group, —N,N—(dialkyl)-amino, —N,N—(w-$R^8$alkyl)$_2$amino wherein $R^8$ is halo or —$OP^{II}$ wherein $P^{II}$ is a protecting group, —NHCOCH$_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —$OP^{III}$ wherein $P^{III}$ is a protecting group the same as $P^I$ or $P^{II}$; $R^6$ and $R^7$ taken together represent the carbon atoms necessary to complete a fused benzene ring; $R^4$, $R^5$ and $R^6$ taken together represent the atoms necessary to complete a fused [ij]quinolizidine ring; and X represents the atoms necessary to complete 2,3-dihydrobenz[d]isothiazole-1,1-dioxide or 2,3-dihydronaphtho[1,8-de]-1,2-thiazine-1,1-dioxide, said $A^1$ and $B^1$ moieties being different.

8. A compound as defined in claim 7 wherein X represents the atoms necessary to complete 2,3-dihydrobenz[d]-isothiazole-1,1-dioxide.

9. A compound as defined in claim 7 wherein said $R^1$ and $R^2$ each are alkyl.

10. A compound as defined in claim 7 wherein said $R^3$ is hydrogen.

11. A compound as defined in claim 7 wherein said $R^1$ and $R^2$ each are alkoxy.

12. A compound as defined in claim 11 wherein said $R^3$ is hydrogen.

13. A compound as defined in claim 10 wherein said $R^5$ is —$OP^I$.

14. A compound as defined in claim 13 wherein said $R^4$ and $R^6$ are alkyl and said $R^7$ is hydrogen.

15. A compound as defined in claim 12 wherein said $R^5$ is —$OP^I$.

16. A compound as defined in claim 15 wherein said $R^4$ and $R^6$ are alkoxy and said $R^7$ is hydrogen.

17. A compound as defined in claim 14 wherein said $R^1$, $R^2$, $R^4$ and $R^6$ each are methyl.

18. A compound as defined in claim 16 wherein said $R^1$, $R^2$, $R^4$ and $R^6$ each are methoxy.

19. A compound as defined in claim 10 wherein said $R^1$ and $R^2$ are methyl and $R^4$, $R^6$ and $R^7$ are hydrogen.

20. A compound as defined in claim 19 wherein said $R^5$ is morpholino.

21. A compound as defined in claim 19 wherein said $R^5$ is —N,N-(dialkyl)amino.

22. A compound as defined in claim 19 wherein said $R^5$ is —N,N-(w-$R^8$alkyl)$_2$amino.

23. A compound as defined in claim 19 wherein said $R^5$ is alkoxy.

24. A compound as defined in claim 19 wherein said $R^5$ is —NHCOCH$_3$.

25. A compound as defined in claim 19 wherein said $R^5$ is pyrrolidino.

26. A compound as defined in claim 19 wherein said $R^5$ is tetrahydro-2H,4H-1,3,6-dioxazocino.

27. A compound as defined in claim 10 wherein said $R^1$ and $R^2$ are methyl, $R^4$ is hydrogen, $R^5$ is —N,N-(dialkyl)-amino and $R^6$ and $R^7$ represent the carbon atoms necessary to complete a fused benzene ring.

28. A compound as defined in claim 10 wherein said $R^1$ and $R^2$ are methyl, $R^4$ and $R^6$ are hydrogen, $R^5$ is —N,N—(dialkyl)amino and $R^7$ is alkyl.

29. A compound as defined in claim 10 wherein said $R^1$ and $R^2$ are methyl, $R^4$, $R^5$ and $R^6$ are hydrogen and $R^7$ is —$OP^{III}$.

30. A compound as defined in claim 12 wherein said $R^1$ and $R^2$ are methoxy, $R^4$ and $R^6$ are hydrogen and $R^5$ and $R^7$ are alkoxy.

31. A compound as defined in claim 7 wherein said $R^1$, $R^2$, $R^3$, $R^4$, $R^5$, $R^6$ and $R^7$ are hydrogen.

32. A compound as defined in claim 7 wherein P, $P^I$, $P^{II}$, and $P^{III}$ are 2'-tetrahydropyranyl, methoxymethyl or dimethyl-t-butylsilyl.

33. The compound

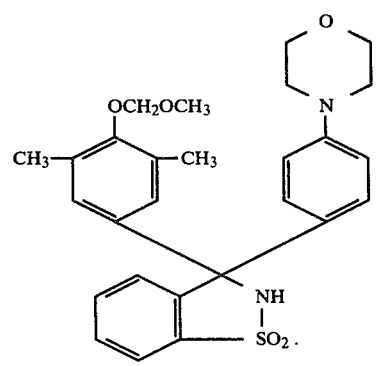

34. The compound

35. The compound
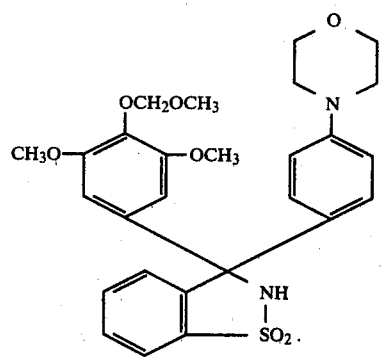
36. The compound
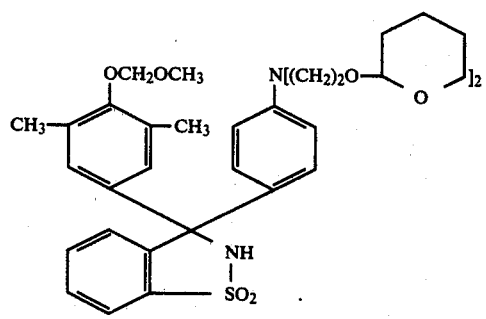
37. The compound
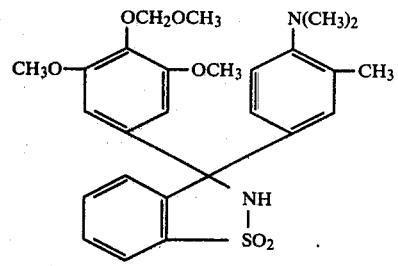
38. The compound
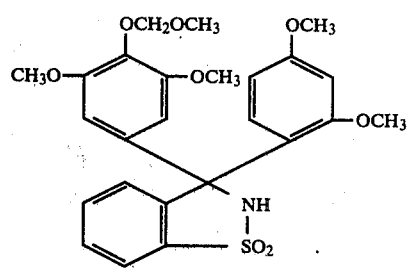
39. The compound
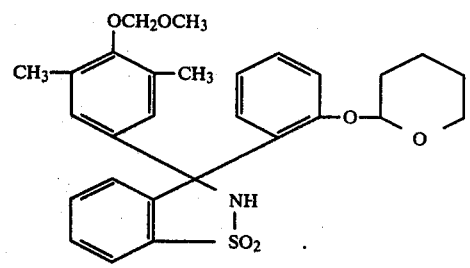
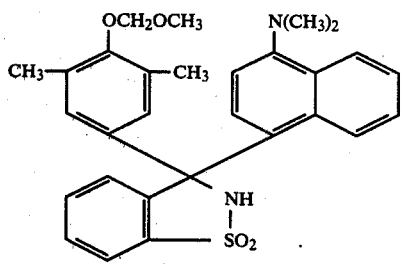
* * * * *